US007118736B2

(12) United States Patent
Cannell et al.

(10) Patent No.: US 7,118,736 B2
(45) Date of Patent: Oct. 10, 2006

(54) HAIR RELAXER COMPOSITIONS COMPRISING AT LEAST ONE HYDROXIDE COMPOUND AND AT LEAST ONE ACTIVATING AGENT, AND METHODS OF USING THE SAME

(75) Inventors: David W. Cannell, Plainfield, NJ (US); Hitendra Mathur, Woodbridge, NJ (US); Nghi Van Nguyen, Edison, NJ (US)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 09/789,667

(22) Filed: Feb. 22, 2001

(65) Prior Publication Data

US 2002/0159962 A1 Oct. 31, 2002

(51) Int. Cl.
*A61Q 5/04* (2006.01)
(52) U.S. Cl. .................................. 424/70.51; 424/70.2
(58) Field of Classification Search ............... 424/70.2, 424/70.51, 70.11
See application file for complete search history.

(56) References Cited

U.S. PATENT DOCUMENTS

| | | | |
|---|---|---|---|
| 2,405,166 A | 8/1946 | Reed et al. | |
| 2,464,280 A | 3/1949 | Reed et al. | |
| 2,464,281 A | 3/1949 | Peterson | |
| 2,564,722 A | 8/1951 | Reed et al. | |
| 2,719,814 A | 10/1955 | Haefele | |
| 3,017,328 A | 1/1962 | Childrey, Jr. et al. | |
| 3,066,077 A | 11/1962 | De Mytt et al. | |
| 3,242,052 A | 3/1966 | Sheffner | |
| 3,243,346 A | 3/1966 | Bechmann et al. | |
| 3,252,866 A | 5/1966 | Sheffner | |
| 3,533,417 A | 10/1970 | Bartoszewicz et al. | |
| 3,654,936 A | 4/1972 | Wajaroff | |
| 3,908,672 A | 9/1975 | Bore et al. | |
| 3,971,391 A | 7/1976 | Bore et al. | |
| 3,973,574 A | 8/1976 | Minagawa, deceased et al. | |
| 4,139,610 A | 2/1979 | Miyazaki et al. | |
| 4,153,681 A | 5/1979 | Shiba | |
| 4,175,572 A | 11/1979 | Hsiung et al. | |
| 4,218,435 A | 8/1980 | Shiba | |
| 4,237,910 A | 12/1980 | Khahil et al. | |
| 4,272,517 A | 6/1981 | Yoneda et al. | |
| 4,303,085 A | 12/1981 | de la Guardia et al. | |
| 4,304,244 A | 12/1981 | de la Guardia | |
| 4,314,572 A | 2/1982 | de la Guardia et al. | |
| 4,322,401 A | 3/1982 | Harada | |
| 4,324,263 A | 4/1982 | de la Guardia | |
| 4,361,157 A | 11/1982 | James | |
| 4,373,540 A | 2/1983 | de la Guardia | |
| 4,390,033 A | 6/1983 | Khalil et al. | |
| 4,416,296 A | 11/1983 | Meyers | |
| 4,424,820 A | 1/1984 | Cannell et al. | |
| 4,509,983 A | 4/1985 | Szabo et al. | |
| 4,605,018 A | 8/1986 | de la Guardia et al. | |
| 4,783,395 A | 11/1988 | Hsieh et al. | |
| 4,793,994 A | 12/1988 | Helioff et al. | |
| 4,816,246 A | 3/1989 | Mathews et al. | |
| 4,859,459 A | 8/1989 | Greiche et al. | 424/71 |
| 4,895,722 A | 1/1990 | Abe et al. | |
| 4,898,726 A | 2/1990 | Beste | |
| 4,950,485 A | 8/1990 | Akhtar et al. | |
| 4,956,175 A | 9/1990 | Maignan et al. | 424/72 |
| 4,992,267 A | 2/1991 | DenBeste et al. | |
| 5,015,767 A | 5/1991 | Maignan et al. | |
| 5,077,042 A | 12/1991 | Darkwa et al. | |
| 5,106,612 A | 4/1992 | Maignan et al. | |
| 5,154,918 A | 10/1992 | Maignan et al. | 424/72 |
| 5,223,252 A | 6/1993 | Kolc et al. | |
| 5,294,230 A | 3/1994 | Wu et al. | |
| 5,332,471 A | 7/1994 | Naddeo et al. | |
| 5,332,570 A | 7/1994 | Bergstrom et al. | |
| 5,348,737 A | 9/1994 | Syed et al. | |
| 5,376,364 A | 12/1994 | Darkwa et al. | |
| 5,419,895 A | 5/1995 | Kubo et al. | |
| 5,523,078 A | 6/1996 | Baylin | |
| 5,565,192 A | 10/1996 | Leroy et al. | |
| 5,565,216 A * | 10/1996 | Cowsar et al. | 424/702 |
| 5,591,425 A | 1/1997 | Dhaliwal | |
| 5,609,859 A | 3/1997 | Cowsar | |
| 5,628,991 A | 5/1997 | Samain et al. | 424/70.1 |
| 5,637,295 A | 6/1997 | Lang et al. | 424/70.2 |
| 5,641,477 A | 6/1997 | Syed et al. | 424/70.4 |
| 5,679,327 A | 10/1997 | Darkwa et al. | |
| 5,679,332 A | 10/1997 | Braun et al. | |
| 5,725,848 A | 3/1998 | Borish et al. | 424/70.5 |
| 5,753,215 A | 5/1998 | Mougin et al. | |

(Continued)

FOREIGN PATENT DOCUMENTS

CN 1138450 A 12/1996

(Continued)

OTHER PUBLICATIONS

Zahn, H. "N,O-peptidyl shift, disulfide exchange and lanthionine formation in wool and other proteins containing cystine," *Chimia (Switz)* 15:378-394 (1961).

(Continued)

*Primary Examiner*—Jyothsan Venkat
(74) *Attorney, Agent, or Firm*—Finnegan Henderson Farabow Garrett & Dunner, L.L.P.

(57) ABSTRACT

A composition for lanthionizing keratin fibers comprising at least one hydroxide compound, with the proviso that said at least one hydroxide compound is not sodium hydroxide, lithium hydroxide or potassium hydroxide; and at least one activating agent chosen from cysteine-based compounds; and methods and kits for use thereof.

26 Claims, No Drawings

U.S. PATENT DOCUMENTS

| | | | |
|---|---|---|---|
| 5,775,342 | A | 7/1998 | Hohenstein et al. |
| 5,824,295 | A | 10/1998 | Syed et al. |
| 5,849,277 | A | 12/1998 | Cowsar |
| 5,872,111 | A | 2/1999 | Au et al. |
| 5,932,201 | A | 8/1999 | de Labbey et al. |
| 5,935,558 | A | 8/1999 | Malle |
| 5,961,667 | A | 10/1999 | Doehling et al. |
| 6,058,943 | A | 5/2000 | Davis-Harris |
| 6,287,582 | B1 | 9/2001 | Gott et al. |
| 6,435,193 | B1 | 8/2002 | Cannell et al. |
| 6,782,895 | B1 | 8/2004 | Van Nguyen et al. |
| 6,792,954 | B1 | 9/2004 | Cannell et al. |
| 2001/0008630 | A1 | 7/2001 | Pyles et al. |
| 2002/0189027 | A1 | 12/2002 | Cannell et al. |

FOREIGN PATENT DOCUMENTS

| | | |
|---|---|---|
| DE | 20 14 628 | 10/1971 |
| DE | 28 23 243 | 11/1979 |
| DE | 3519463 A1 | 12/1986 |
| DE | 4326974 A1 | 5/1994 |
| EP | 0 465 342 A | 1/1992 |
| EP | 0 636 358 | 2/1995 |
| EP | 0 667 141 A | 8/1995 |
| EP | 0 712 623 | 5/1996 |
| GB | 1002889 | 9/1965 |
| GB | 1 281 662 | 7/1972 |
| JP | A S50-029756 | 3/1975 |
| JP | A S50-029757 | 3/1975 |
| JP | 51 9013 | 3/1976 |
| JP | A S63-190814 | 8/1988 |
| JP | A H02-104515 | 4/1990 |
| JP | A H04-243860 | 8/1992 |
| JP | A H04-295413 | 10/1992 |
| JP | A H5-39211 | 2/1993 |
| JP | A H05-246827 | 9/1993 |
| JP | A H6-172141 | 6/1994 |
| JP | A H6-343511 | 12/1994 |
| JP | A H7-101840 | 4/1995 |
| JP | A H08-245559 | 9/1996 |
| JP | A 2002-003346 | 1/2002 |
| JP | A 2002-68976 | 3/2002 |
| WO | WO 87/05500 | 9/1987 |
| WO | WO 89 06122 A | 7/1989 |
| WO | WO 93 01791 A | 2/1993 |
| WO | 0667141 A2 | 8/1995 |
| WO | WO 97/07775 | 3/1997 |
| WO | WO 99/18922 | 4/1999 |
| WO | WO 01/64171 A2 | 9/2001 |
| WO | WO 01 74318 A | 10/2001 |
| WO | WO 02/67875 A1 | 9/2002 |

OTHER PUBLICATIONS

International Search Report for International Application No. PCT/US02/03392.
Schoon, Douglas D., "Hair structure and chemistry simplified", Revised edition, pp. 191-192, Milady Publishing Co. (1993).
Robbins, Clarence R., "Chemical and physical behavior of human hair", pp. 124-126, 148-151, and 162-163, Springer (2002).
English translation of Hair Science: Japan Hair Science Assoc., Jan. 10, 1996, 2nd. Ed., p. 87.
Office Action dated Dec. 5, 2005, in co-pending Application No. 09/931,912.
English language Derwent Abstract for CN 1138450 A.
English language Derwent Abstract for JP-A 2002-003346.
English language Derwent Abstract for JP-A 2002-68976.
English language Derwent Abstract for JP-A H6-172141.
English language Derwent Abstract for JP-A H7-101840.
Hair Science: Japan Hair Science Assoc., Jan. 10, 1996, 2nd. Ed., p. 87.
Office Action dated Aug. 31, 2005, in co-pending Application No. 09/931,913.
Clariant, "Tylose Water-soluble cellulose ethers", Product range and fields of Application.
Co-pending U.S. Appl. No. 09/516,942—Title: Hair Relaxer Compositions Utlilizing Complexing Agent Activators Inventors: Nghi Van Nguyen et al. U.S. Filing Date: Mar. 1, 2000.
Co-pending U.S. Appl. No. 09/717,206—Title: Hair Relaxer Compositions Utlilizing Cation Exchange Compositions Inventors: David W. Cannell et al. U.S. Filing Date: Nov. 22, 2001.
Co-pending U.S. Appl. No. 09/931,912—Title: Compositions Comprising at Least One Hydroxide Compound and at Least One Reducing Agent, and Methods for Relaxing Inventors: Nghi Van Nguyen et al. U.S. Filing Date: Aug. 20, 2001.
Co-pending U.S. Appl. No. 09/931,913—Title: Compositions Comprising at Least One Hydroxide Compound and at Least One Oxidizing Agent, and Methods for Relaxing Inventors: Nghi Van Nguyen et al. U.S. Filing Date: Aug. 20, 2001.
Co-pending U.S. Appl. No. 09/931,914—Title: Compositions Comprising at Least One Hydroxide Compound and at Least One Complexing Agent, and Methods for Using the Same Inventors: Nghi Van Nguyen et al. U.S. Filing Date: Aug. 20, 2001.
Co-pending U.S. Appl. No. 09/931,919—Title: Method for Relaxing and Re-Waving Hair Comprising at Least One Reducing Agent and at Least One Hydroxide Compound Inventors: David W. Cannell et al. U.S. Filing Date: Apr. 20, 2001.
Co-pending U.S. Appl. No.10/214,942—Title: Hair Relaxer Compositions Utilizing Cation Exchange Composition.
English language Derwent Abstract for DE 20 14 628.
English language Derwent Abstract for DE 28 23 243.
English language Derwent Abstract for EP 0 636 358.
English language Derwent Abstract for JP 76-09013.
Examiner's Answer dated Jun. 13, 2005, in co-pending U.S. Appl. No. 09/838,197.
International Search Report for International Application No. PCT/US01/43193, Jul. 5, 2002, Examiner Simon.
International Search Report for International Application No. PCT/US02/08270, Aug. 7, 2002, Ex. Bertrand.
International Search Report for International Application No. PCT/US02/21846, Nov. 8, 2002, Ex. Marie.
International Search Report for International Application No. PCT/US02/21848, Nov. 25, 2002, Examiner Bertrand.
International Search Report for International Application No. PCT/US02/21849, May 26, 2003, Examiner Menidjel.
Office Action dated Apr. 13, 2004, in co-pending U.S. Appl. No. 09/931,913.
Office Action dated Apr. 28, 2003, in co-pending U.S. Appl. No. 09/931,914.
Office Action dated Aug. 6, 2003, in co-pending U.S. Appl. No. 09/838,197.
Office Action dated Dec. 16, 2003, in co-pending U.S. Appl. No. 10/214,942.
Office Action dated Feb. 6, 2003, in co-pending U.S. Appl. No. 09/838,197.
Office Action dated Jul. 22, 2004, in co-pending U.S. Appl. No. 09/838,197.
Office Action dated Jul. 23, 2004, in co-pending U.S. Appl. No. 09/931,913.
Office Action dated Mar. 8, 2005, in co-pending U.S. Appl. No. 09/931,912.
Office Action dated May 24, 2004, in co-pending U.S. Appl. No. 09/931,912.
Office Action dated Nov. 19, 2004, in co-pending U.S. Appl. No. 09/931,913.
Office Action dated Oct. 27, 2003, in co-pending U.S. Appl. No. 09/931,913.
Office Action dated Oct. 27, 2003, in co-pending U.S. Appl. No. 09/931,912.
Office Action dated Sep. 9, 2003, in co-pending U.S. Appl. No. 09/931,914.
Office Action dated Sep. 10, 2002, in co-pending U.S. Appl. No. 09/789,667.
Ogawa et al., "A Curing Method for Permanent Hair Straightening using Thioglycolic and Dithioglycolic Acids", J. Cosmet. Sci., 51. 379-399 (Nov./Dec. 2000).
Zviak, C., The Science of Hair Care, pp. 185-186 (1986).

* cited by examiner

HAIR RELAXER COMPOSITIONS COMPRISING AT LEAST ONE HYDROXIDE COMPOUND AND AT LEAST ONE ACTIVATING AGENT, AND METHODS OF USING THE SAME

The present invention relates to methods for lanthionizing keratin fibers using a combination of at least one "no-lye" hydroxide compound and at least one activating agent chosen from cysteine-based compounds. The at least one activating agent can sufficiently activate the at least one hydroxide compound to effect lanthionization of the keratin fibers. In one embodiment, the process of lanthionizing keratin fibers may result in relaxed or straightened hair. The invention is also directed to compositions for straightening or relaxing hair comprising at least one "no-lye" hydroxide compound and at least one cysteine-based activating agent.

Straightening or relaxing the curls of very curly hair may increase the manageability and the ease of styling such hair. In today's market, there is an increasing demand for hair care products referred to as "hair relaxers" which can relax or straighten naturally curly or kinky hair. Hair relaxers may either be applied in a hair salon by a professional or in the home by the individual consumer.

Hair fiber is a keratinous material which is comprised of proteins. Many of the polypeptides in hair fibers are bonded together by disulfide bonds (—S—S—). A disulfide bond may be formed from the reaction of the two sulfhydryl groups (—SH) one on each of two cysteine residues which results in the formation of a cystine residue. While there may be other types of bonds between the polypeptides in hair fibers, such as ionic bonds, the permanent curling and the shape of the hair is essentially dependent on the disulfide bonds of cystine residues.

Generally, hair relaxing processes are chemical processes which may alter the aforementioned disulfide bonds between polypeptides in hair fibers and may form lanthionine residues $[S[CH_2CH(NH-)(CO-)]_2]$. Thus, the term "lanthionizing" is used when one skilled in the art refers to the relaxing or straightening of keratin fibers by hydroxide ions.

For example, hair fibers may be relaxed or straightened by disrupting the disulfide bonds of the hair fibers with an alkaline reducing agent. The chemical disruption of disulfide bonds with such an agent is generally combined with mechanical straightening of the hair, such as combing, and straightening generally occurs due to changes in the relative positions of neighboring polypeptide chains within the hair fiber. This reaction is generally terminated by rinsing and/or application of a neutralizing composition.

The reaction with the alkaline agent is normally initiated by available hydroxide ions. As used herein, "available hydroxide ions" are hydroxide ions which are available for lanthionization. Not to be limited by theory, there are two reaction sequences that are predominantly used in the art to explain the disruption of the disulfide bonds in hair fibers by available hydroxide ions. Both of these reaction sequences result in lanthionine residue formation. One reaction sequence comprises at least one bimolecular nucleophilic substitution reaction wherein an available hydroxide ion directly attacks the disulfide linkage of a cystine residue. The result is the formation of lanthionine residues and HOS—. See Zviak, C., The Science of Hair Care, 185–186 (1986). The second reaction sequence comprises at least one β-elimination reaction initiated by the nucleophilic attack of an available hydroxide ion on a hydrogen atom bonded to a carbon atom that is in the β-position with respect to the disulfide bond of a cystine residue. See Zviak. The result is the formation of a dehydroalanine residue. The dehydroalanine residue then reacts with either the thiol group of a cysteine residue or the amino group of an alanine residue to form a lanthionine residue or a lysinoalanine residue, respectively. These stable irreversible crosslinks in the treated hair make subsequent chemical re-linking of the polypeptides unnecessary. Thus, the only step that may be required following a straightening process using such hydroxide-containing alkaline agents is the removal of any excess alkaline solution to avoid and minimize damage to the hair protein or skin. If such a step is required, an acidic shampoo may be used to neutralize residual alkali and remove it from the hair and scalp.

Hydroxide-containing alkaline agents also have other advantages. For example, alkaline agents, such as guanidine hydroxide, do not have a highly objectionable odor or cause such an odor on treating the hair. Further, hydroxide-based straighteners generally have relatively fast processing times and good straightening of naturally curly or kinky hair. Additionally, the achieved straightening effect is more permanent; i.e., less likely to revert to a curly state after shampooing and wearing than is hair straightened with some other straighteners.

Despite these advantages, certain hydroxide-containing alkaline agents may have disadvantages. These disadvantages may be heightened when the hydroxide-containing alkaline agent is sodium hydroxide. Specifically, the causticity of sodium hydroxide can adversely affect the condition of the hair, for example, leaving it in a brittle state and harsh to the touch. Additionally, prolonged or unnecessary exposure of hair to such a strong alkali can weaken, break and dissolve the hair. In some instances, such a strong alkali can discolor the natural color of the hair. For example, the tone of natural brown hair may be reddened and natural white or grey hair may be yellowed. Further, the natural sheen of the hair may be delustered.

Most frequently, commercial relaxing compositions are in the form of gels or emulsions that contain varying proportions of strong water-soluble bases, such as sodium hydroxide (NaOH), or of compositions that contain slightly-soluble metal hydroxides, such as calcium hydroxide ($Ca(OH)_2$), which can be converted in situ to soluble bases, such as guanidine hydroxide. Traditionally, the two main hair relaxers used in the hair care industry for generating hydroxide ions are referred to as "lye" (lye=sodium hydroxide) relaxers and "no lye" relaxers.

The "lye" relaxers generally comprise sodium hydroxide in a concentration ranging from 1.5% to 2.5% by weight relative to the total weight of the composition (0.38M –0.63 M) depending on the carrier used, the condition of the hair fibers and the desired length of time for the relaxation process.

While "no lye" relaxers may not contain lye, they may nonetheless rely on the soluble hydroxides of inorganic metals, such as potassium hydroxide and lithium hydroxide. Other "no lye" relaxers may use hydroxide ions obtained, for example, from a slightly-soluble source, such as $Ca(OH)_2$. For example, the slightly soluble $Ca(OH)_2$ may be mixed with guanidine carbonate to form guanidine hydroxide, a soluble but unstable source of hydroxide, and insoluble calcium carbonate ($CaCO_3$). This reaction is driven to completion by the precipitation of $CaCO_3$ and is, in effect, substituting one insoluble calcium salt for a slightly soluble calcium salt. Because guanidine hydroxide is unstable, the components are stored separately until the time of their use.

In commercial products based on guanidine hydroxide, the concentration of guanidine carbonate used is generally at least 5.8% by weight relative to the total weight of the final mixture. Significantly, it is known that relaxers derived from guanidinium hydroxide are inherently less irritating to the skin and scalp than those deriving from alkali metal hydroxides. See U.S. Pat. No. 5,849,277, the disclosure of which is incorporated herein by reference.

Although generally gentler on the hair, guanidine carbonate and calcium hydroxide may create a different set of problems. The insoluble byproduct, $CaCO_3$, can leave a white residue or unattractive "whitening" or "ashing." This residue remains in the hair since divalent metals such as calcium have a relatively good affinity for keratin. A decalcifying shampoo may be subsequently needed to remove the ashing.

This ashing may be especially problematic when using strong commercial hair relaxers which generally comprise a high concentration of both guanidine carbonate and calcium hydroxide. For example, according to U.S. Pat. No. 5,679,327, the disclosure of which is incorporated herein by reference, to achieve permanent hair relaxation, for example of coarse and resistant hair, the amount of calcium hydroxide should generally range from 4% to 10% by weight and the amount of guanidine carbonate should generally be 28% by weight.

Reducing agents, such as thiol-containing compounds, may also relax or straighten hair by disrupting the disulfide bonds of the hair fibers. Processes comprising the application of these reducing agents generally require two steps: (1) a reducing step comprising the use of the reducing agent, and (2) a neutralizing step comprising the use of an oxidizing composition.

These agents may have disadvantages not present with alkaline agents. For example, thiol-based straightening or relaxing may require the use of an oxidizing neutralizer, such as hydrogen peroxide, to chemically relink the hair keratin disulfide bonds and stop the straightening process quickly. As the thiol-reduced hair is in an alkaline state, any excess neutralizer must also be removed to avoid bleaching the natural color of the hair. Further, thiol-reduced hair may emit an offensive odor.

The reaction with the reducing agent is normally initiated by thiolate ions. Generally, the higher the concentration of the thiolate ions in the composition, the faster the straightening or relaxing reaction will occur. See Zviak at page 190. This concentration, and therefore the rate of the reaction, are dependent on the ionization constant $K_I$ of the thiol used. Thus, the pK value of a particular thiol expresses the nature of the thiol and determines both the equilibrium level and, therefore, the concentration of thiolate ions at a given pH.

Cysteine is a sulfur-containing amino acid having an available polar sulfhydryl functional group as well as with polar amino and carboxy acid groups. In the free base form, also called cysteine base, the structural formula is $HSCH_2CH(NH_2)COOH$, which has reported dissociation constants (pK) of $pK_1$ 1.71, $pK_2$ 8.33, and $pK_3$ 10.78. Cysteine and cysteine-derived compounds are substantially odorless and acceptable hair keratin disulfide reducing agents. As the pK of cysteine is relatively high, cysteine may only be capable of efficiently straightening or relaxing hair at a high pH. See Zviak at page 191. For example, at a highly alkaline pH generally ranging from 12 to 14, the polar sulfhydryl functional group (—SH) is ionizable, that is, it forms a thiolate ion (—$S^\ominus$).

On the other hand, cysteine is generally thought of as a "weak" reducing agent. See Zviak at page 192. Therefore, cysteine used as a main hair-straightening or relaxing agent may have certain disadvantages. For example, relatively high amounts of upwards of 3% to 20% by weight of cysteine (or a cysteine derivative) are reportedly required to effect a beneficial change in the configuration of the hair. Like other sulfhydryl compounds, cysteine acts on the cystine disulfide bonds in hair keratin, so the treated hair must be chemically neutralized to re-link the hair keratin disulfide bonds. In addition, cysteine oxidizes readily to insoluble cystine which can deposit as crystals on the skin and form a dulling film on the hair.

The reported useful pH of various compositions containing cysteine or cysteine derivatives in the literature generally ranges from pH 6 to about pH 11. However, to minimize skin irritation and maximize the action of the cysteine or its derivatives on hair, a pH of 10 or less is usually required. Sodium hydroxide has been disclosed as a cosmetically acceptable inorganic base to adjust the alkalinity of some of the foregoing compositions reported in the literature. However, volatile ammonium hydroxide and organic amine bases are generally prepared, and the amount of sodium hydroxide, if used, to adjust the pH is rather miniscule. For example, it is known that a solution of sodium hydroxide at 0.05% by weight has a pH of 12. Thus, even if some sodium hydroxide were available as free base at a pH of 11, the amount present would be too low to straighten hair. It is also known that sodium hydroxide at below pH 12 and at a titratable alkalinity of less than 0.5% by weight effects substantially no straightening of curly hair. Thus, cysteine and other water-soluble cysteine derived compounds have not provided a viable alternative to sodium hydroxide-based hair straightening.

Some strides have been made to improve the condition of sodium hydroxide-straightened hair by incorporating an auxiliary hair keratin disulfide reducing agent having a sulfhydryl functional group available chosen from cysteine, homologs of cysteine, and water soluble derivatives of cysteine. See, for example, U.S. Pat. No. 4,992,267, the disclosure of which is incorporated herein by reference. This patent discloses the use of sodium hydroxide at concentrations of between about 1 weight percent to about 2.5 weight percent, preferably between about 1.5 weight percent and about 2.25 weight percent relative to the total concentration of the composition. Therefore, there is still a need for a no-lye-based hair relaxing or straightening composition which is able to generate relatively low concentrations of available hydroxide ions for use in a no-lye process, and yet retain beneficial hair relaxing or straightening effects equivalent to or better than those obtained from the higher amounts of available hydroxide ions presently used. An ideal no-lye, hydroxide-based hair relaxing and/or straightening composition, process and kit would also provide a relatively fast processing time and good hair condition.

The present invention, in one aspect, provides methods for lanthionizing keratin fibers by using a composition comprising at least one hydroxide compound with the proviso that said at least one hydroxide compound is not sodium hydroxide, lithium hydroxide or potassium hydroxide and at least one activating agent chosen from cysteine-based compounds.

The inventors have discovered that by combining at least one "no-lye" hydroxide compound, such as guanidine hydroxide, with at least one activating agent chosen from cysteine-based compounds, it may be possible to decrease the amount of the at least one hydroxide compound needed while maintaining good hair condition.

Specifically, one embodiment of the present invention is directed to a method for lanthionizing keratin fibers to achieve straightening or relaxation of the keratin fibers comprising generating available hydroxide ions in at least one solvent comprising combining in the at least one solvent at least one hydroxide compound and at least one activating agent chosen from cysteine-based compounds, applying a composition comprising the generated available hydroxide ions to keratin fibers for a sufficient period of time to lanthionize the keratin fibers, and terminating the lanthionization when a desired level of straightening or relaxation of the keratin fibers has been reached, with the proviso that said at least one hydroxide compound is not sodium hydroxide, lithium hydroxide or potassium hydroxide. The at least one hydroxide may be added to the at least one activating agent or vice versa. The keratin fibers may be human keratin fibers, such as hair.

Another embodiment of the present invention is directed to a composition for lanthionizing keratin fibers comprising at least one hydroxide compound with the proviso that said at least one hydroxide compound is not sodium hydroxide, lithium hydroxide or potassium hydroxide and at least one activating agent chosen from cysteine-based compounds. In another embodiment, the at least one hydroxide compound is chosen from alkali metal hydroxides, alkaline earth metal hydroxides, transition metal hydroxides, lanthanide metal hydroxides, actinide metal hydroxides, Group III hydroxides, Group IV hydroxides, Group V hydroxides, Group VI hydroxides, organic hydroxides, and compounds comprising at least one hydroxide substituent which is at least partially hydrolyzable, with the proviso that said at least one hydroxide compound is not sodium hydroxide, lithium hydroxide or potassium hydroxide.

The invention also provides for multicomponent kits for lanthionizing keratin fibers. In one embodiment, the kit comprises at least two separate compartments, wherein one compartment of the kit contains a composition for generating available hydroxide ions that comprises at least one hydroxide compound while the other compartment of the kit contains at least one activating agent chosen from cysteine-based compounds.

Reference will now be made in detail to exemplary embodiments of the present invention. Not to be limited as to theory, the lanthionization of keratin fibers is believed to be driven by the release of hydroxide ions which disrupt the disulfide bonds of cystine residues in the fibers. The compositions of the present invention may offer at least one advantage over traditional "lye" and "no lye" hair relaxers, for example, by providing a faster and novel way of generating sufficient available hydroxide ions from "no lye" hydroxide compounds to effectively relax and/or straighten the hair with lower concentrations of hydroxide compounds.

As described above, the hair relaxing compositions of the prior art utilized soluble or slightly soluble metal hydroxides. Slightly soluble metal hydroxides may not be soluble enough in water to generate a sufficient concentration of available hydroxide ions to effect lanthionization of keratin fibers. For example, the hydrolysis reaction of divalent metal hydroxides can be represented by the following reaction scheme, in which the equilibrium favors the left side of the reaction:

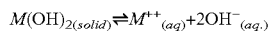

$$M(OH)_{2(solid)} \rightleftharpoons M^{++}_{(aq)} + 2OH^-_{(aq.)}$$

In traditional relaxers containing slightly soluble metal hydroxides, the equilibrium was normally pushed to the right side of the equilibrium, and therefore the reaction was driven to completion, by the precipitation of $M^{++}$ in the form of an insoluble compound such as $CaCO_3$.

The composition and methods of the present invention may have several benefits and advantages versus the traditional relaxers described above. One such potential benefit is that the relaxing or straightening effect usually obtained with relatively low concentrations of hydroxide ion-based hair relaxers and straighteners may be enhanced to a level approximating or equivalent to that obtained with high concentrations without at least one of the aforementioned problems. The effectiveness of the at least one hydroxide compound as a relaxer or straightener may be augmented by including at least one activating agent chosen from cysteine-based compounds while retaining good hair condition. Surprisingly, when relatively low amounts of the at least one activating compound were included in a "no-lye" composition comprising at least one hydroxide compound as defined herein, the relaxing or straightening effect normally achieved, especially with a relatively low amount of the at least one hydroxide compound, was noticeably improved.

Another benefit is that the natural color of the pre-straightened hair may be substantially retained after relaxing or straightening, thereby overcoming any discoloration problems which may be associated with highly alkaline hair relaxing or straightening compositions. Further, when the present invention is employed, formation of cystine may not be observed on the hair, the skin and/or in solution. Still another benefit is that skin irritation problems which may be associated with the relatively high concentration of available hydroxide ions which may be required for effective straightening or relaxation of the hair may be avoided.

Therefore, by using at least one activating agent of the present invention, "lye" relaxers are not used and a lower concentration of at least one "no lye," hydroxide compound may be used without sacrificing effectiveness, may improve hair condition.

Further, the chemical reactivity of the inventive compositions may be stopped by a rinsing step with water, thereby reducing or even eliminating post-rinsing chemical action. Therefore, the condition of hair relaxed using the inventive method may be better than the condition of hair relaxed using commercial hydroxide-based relaxers, such as those employing as a relaxing agent sodium hydroxide. As used herein, "condition of hair" refers to at least one subjective property of hair such as, for example, luster, color, tactile properties and tensile fiber properties (such as those reflected by fiber breakage and visibly straighter hair). As used herein, "tensile fiber properties" includes physical and chemical characteristics of human hair such as, for example, those associated with intact fiber integrity (which may contribute to desirable mechanical properties of good hair condition, such as, for example, combability, manageability and softness to the touch).

According to the present invention, the at least one hydroxide compound can be chosen from alkali metal hydroxides, alkaline earth metal hydroxides, transition metal hydroxides, lanthanide metal hydroxides, actinide metal hydroxides, Group III hydroxides, Group IV hydroxides, Group V hydroxides, Group VI hydroxides, organic hydroxides, and compounds comprising at least one hydroxide substituent which is at least partially hydrolyzable, with the proviso that the at least one hydroxide compound is not sodium hydroxide, lithium hydroxide or potassium hydroxide. Non-limiting examples of the at least one hydroxide compound include rubidium hydroxide, cesium hydroxide, francium hydroxide, beryllium hydroxide, magnesium hydroxide, calcium hydroxide, strontium hydroxide, barium hydroxide, cupric hydroxide, molybdenum hydroxide, manganese hydroxide, zinc hydroxide, cobalt hydroxide, nickel hydroxide, cadmium hydroxide, gold hydroxide, lanthanum hydroxide, cerium hydroxide, actinium hydroxide, thorium hydroxide, aluminum hydroxide, guanidine hydroxides and quaternary ammonium hydroxides. The at least one hydroxide compound can also be chosen from those formed in situ, such as, for example, guanidine hydroxide. As previously mentioned, guanidine hydroxide may be formed in situ, for example, from the reaction of calcium hydroxide and guanidine carbonate. In one embodiment, the at least one hydroxide compound is unsubstituted guanidine hydroxide.

According to the present invention, the at least one activating agent is chosen from cysteine-based compounds. The cysteine-based compounds can be chosen from their D-form, L-form, DL-form and mixtures of any of the foregoing. In one embodiment, the at least one activating agent is chosen from cysteine, optionally substituted; homologs of cysteine, optionally substituted; derivatives of cysteine, optionally substituted; and salts of any of the foregoing chosen from carboxylate salts, amine salts and carboxylate and amine salts. As used herein, the term "carboxylate salts" refers to salts of at least one carboxylic acid functional group. Similarly, as used herein, the term "amine salts" refers to salts of at least one amino functional group. Further, as used herein, the term "carboxylate and amine salts" refers to salts of both at least one carboxylic acid functional group and at least one amino functional group.

Non-limiting examples of homologs of cysteine are homocysteine, homocysteine hydrate, and salts of any of the foregoing chosen from amine salts, carboxylate salts and carboxylate and amine salts. Non-limiting examples of substituted derivatives of cysteine are N-substituted derivatives of cysteine (such as N-acetyl-L-cysteine and N-carbamoylcysteine), N-alkanoylcysteines (such as N-propionylcysteine, N-butyrylcysteine, N-valerylcysteine, N-caproylcysteine and N-heptanoylcysteine), N-substituted aroylcysteines (such as N-benzoylcysteine, N-toluoylcysteine, N-(ethylbenzyl)cysteine and N-(propylbenzoyl) cysteine), amides of N-acylated cysteine (such as 2-acetamide-3-mercaptopropionamide), alkyl esters of cysteine (such as cysteine methyl ester, cysteine ethyl ester and cysteine propyl ester), and salts of any of the foregoing chosen from amine salts, carboxylate salts and carboxylate and amine salts. In one embodiment, the N-alkanoyl groups in the N-alkanoylcysteines are chosen from alkanoyl groups comprising from 1 to 10 carbon atoms. In one embodiment, the alkyl groups in the alkyl esters of cysteine are chosen from alkyl groups comprising from 1 to 4 carbon atoms.

In one embodiment, the at least one activating agent is chosen from cysteine-based compounds which comprise at least one unsubstituted thiol group, cysteine-based compounds which comprise at least one protected thiol group wherein the at least one protected thiol group is de-protected upon hydrolysis, and salts of any of the foregoing chosen from amine salts, carboxylate salts and carboxylate and amine salts. For example, cysteine-based compounds can be chosen from those in which the sulfhydryl functional group of cysteine is indirectly available for reaction in that it becomes available upon hydrolysis in water or at an alkaline pH. For example, the cysteine-based compounds which comprise at least one protected thiol group wherein the at least one protected thiol group is de-protected upon hydrolysis can be chosen from homocysteine thiolactone, N-alkanoyl substituted derivatives of homocysteine thiolactone, N-aroyl substituted derivatives of homocysteine thiolactone, and salts thereof chosen from amine salts, carboxylate salts and carboxylate and amine salts. Non-limiting examples of N-aroyl substituted derivatives of homocysteine thiolactone include N-toluoyl homocysteine thiolactone, and N-(ethyl benzyl) homocysteine thiolactone. Non-limiting examples of N-alkanoyl substituted derivatives of homocysteine thiolactone include N-methyl homocysteine thiolactone, N-ethyl homocysteine thiolactone, N-propyl homocysteine thiolactone and N-butyl homocysteine thiolactone and salts of any of the foregoing chosen from amine salts, carboxylate salts and carboxylate and amine salts.

Descriptions of some of the foregoing compounds and their chemical properties as hair keratin disulfide reducing agents in less alkaline (e.g. less than pH 10) compositions can be found in U.S. Pat. Nos. 4,272,517, 3,242,052, 3,252,866, 4,153,681 and 4,218,435, the disclosures of which are incorporated herein by reference. The pH of the present compositions may, for example, range from pH 12 to pH 14.

The at least one activating agent can be present in the composition in a molar ratio of available hydroxide ions to the at least one activating agent generally ranging from 4:1 to 14:1. As used herein, the amount of available hydroxide ions sufficient to realize lanthionization is defined in terms of the molar ratio of available hydroxide ions to total hydroxide ions. According to the present invention, the amount of available hydroxide ions generally ranges from 0.02 mol to 0.04 mol per 100 g of the composition (i.e., the final mixture).

As previously mentioned, the at least one hydroxide compound can be chosen from those formed in situ. Additionally, in one embodiment, the inventive composition further comprises at least one compound capable of being converted in situ to at least one soluble base. In this case, the at least one hydroxide compound formed in situ is derived from the reaction of at least one compound capable of being converted in situ to at least one soluble base and the at least one hydroxide compound. For example, the composition may comprise at least one hydroxide compound, such as calcium hydroxide, at least one activating agent chosen from cysteine-based compounds, such as cysteine, in a molar ratio of available hydroxide ions to the at least one activating agent generally ranging from 4:1 to 14:1, and at least one compound capable of being converted in situ to at least one soluble base, such as guanidine carbonate, in an amount sufficient to yield 0.02 mol to 0.04 mol of available hydroxide ions per 10 g of said composition. Thus, the reaction of calcium hydroxide (the at least one hydroxide compound) with guanidine carbonate (the at least one compound capable of being converted in situ to at least one soluble base) forms guanidine hydroxide (the at least one hydroxide compound formed in situ).

According to the present invention, the at least one solvent can be chosen from solvents commonly used in compositions for the hair. Non-limiting examples of the at least one solvent include water and solvents which may lower the ionic bonding forces in the solute molecules enough to cause at least partial separation of their constituent ions, such as dimethyl sulfoxide (DMSO). In one embodiment, the at least one solvent is chosen from water and DMSO. The at least one solvent can be present in an amount sufficient to ensure that, upon mixing, enough of the generated available hydroxide ions remain soluble in order to effect lanthionization of keratin fibers.

According to the present invention, the composition can be in the form of an oil-in-water emulsion, a water-in-oil emulsion, a dispersion or a suspension. Further, the composition can be in the form of a cream, a foam, a gel, a spray, a powder or a liquid.

Another subject of the present invention is a method for lanthionizing keratin fibers comprising (a) storing a first composition, (b) storing a second composition separately from the first composition, (c) combining the first composition with the second composition, and (d) applying the composition to the keratin fibers for a sufficient period of time to achieve a desired relaxation. The first composition comprises at least one activating agent chosen from cysteine-based compounds and optionally at least one entity chosen from (1) at least one compound capable of being converted in situ to at least one soluble base and (2) at least one hydroxide compound chosen from alkali metal hydroxides, alkaline earth metal hydroxides, transition metal hydroxides, lanthanide metal hydroxides, actinide metal hydroxides, Group III hydroxides, Group IV hydroxides, Group V hydroxides, Group VI hydroxides, organic hydroxides, and compounds comprising at least one hydroxide substituent which is at least partially hydrolyzable, with the proviso that the at least one hydroxide compound is not sodium hydroxide, lithium hydroxide or potassium hydroxide. The second composition comprises at least one entity chosen from (1) at least one compound capable of being converted in situ to at least one soluble base and (2) at least one hydroxide compound chosen from alkali metal hydroxides, alkaline earth metal hydroxides, transition metal hydroxides, lanthanide metal hydroxides, actinide metal hydroxides, Group III hydroxides, Group IV hydroxides, Group V hydroxides, Group VI hydroxides, organic hydroxides, and compounds comprising at least one hydroxide substituent which is at least partially hydrolyzable, with the proviso that the at least one hydroxide compound is not sodium hydroxide, lithium hydroxide or potassium hydroxide. Thus, the at least one compound capable of being converted in situ to at least one soluble base and at least one hydroxide compound are present, together or separately, in at least one composition chosen from the first composition and the second composition.

Yet another subject of the present invention is a method for lanthionizing keratin fibers comprising (a) storing a first composition, (b) storing a second composition separately from the first composition, (c) storing a third composition separately from the first composition and the second composition, (d) combining the first composition with the second composition and the third composition, and (e) applying the composition to the keratin fibers for a sufficient period of time to achieve a desired relaxation, wherein the first composition comprises at least one activating agent chosen from cysteine-based compounds, wherein the second composition is chosen from at least one compound capable of being converted in situ to at least one soluble base and wherein the third composition comprises at least one hydroxide compound chosen from alkali metal hydroxides, alkaline earth metal hydroxides, transition metal hydroxides, lanthanide metal hydroxides, actinide metal hydroxides, Group III hydroxides, Group IV hydroxides, Group V hydroxides, Group VI hydroxides, organic hydroxides, and compounds comprising at least one hydroxide substituent which is at least partially hydrolyzable, with the proviso that the at least one hydroxide compound is not sodium hydroxide, lithium hydroxide or potassium hydroxide.

The present invention also provides a multicomponent kit for relaxing keratin fibers comprising at least two compartments. A first compartment contains at least one hydroxide compound chosen from alkali metal hydroxides, alkaline earth metal hydroxides, transition metal hydroxides, lanthanide metal hydroxides, actinide metal hydroxides, Group III hydroxides, Group IV hydroxides, Group V hydroxides, Group VI hydroxides, organic hydroxides, and compounds comprising at least one hydroxide substituent which is at least partially hydrolyzable, with the proviso that the at least one hydroxide compound is not sodium hydroxide, lithium hydroxide or potassium hydroxide. A second compartment contains at least one activating agent chosen from cysteine-based compounds. In one embodiment, the at least one hydroxide compound is unsubstituted guanidine hydroxide. In another embodiment, the at least one activating agent is cysteine.

The present invention also provides a multicomponent kit for relaxing keratin fibers, wherein the kit comprises at least three compartments. In one embodiment, a first compartment contains at least one hydroxide compound chosen from alkali metal hydroxides, alkaline earth metal hydroxides, transition metal hydroxides, lanthanide metal hydroxides, actinide metal hydroxides, Group III hydroxides, Group IV hydroxides, Group V hydroxides, Group VI hydroxides, organic hydroxides, and compounds comprising at least one hydroxide substituent which is at least partially hydrolyzable with the proviso that the at least one hydroxide compound is not sodium hydroxide, lithium hydroxide or potassium hydroxide; a second compartment contains at least one compound capable of being converted in situ to at least one soluble base; and a third compartment contains at least one activating agent chosen from cysteine-based compounds. A non-limiting example of the at least one at least one compound capable of being converted in situ to at least one soluble base is guanidine carbonate, wherein the at least one soluble base may be guanidine hydroxide. In another embodiment, the at least one activating agent is cysteine.

Another subject of the present invention is a multicompartment kit comprising at least two compartments. A first compartment contains at least one activating agent chosen from cysteine-based compounds and optionally at least one entity chosen from (1) at least one compound capable of being converted in situ to at least one soluble base and (2) at least one hydroxide compound chosen from alkali metal hydroxides, alkaline earth metal hydroxides, transition metal hydroxides, lanthanide metal hydroxides, actinide metal hydroxides, Group III hydroxides, Group IV hydroxides, Group V hydroxides, Group VI hydroxides, organic hydroxides, and compounds comprising at least one hydroxide substituent which is at least partially hydrolyzable, with the proviso that the at least one hydroxide compound is not sodium hydroxide, lithium hydroxide or potassium hydroxide. A second compartment comprises at least one entity chosen from (1) at least one compound capable of being converted in situ to at least one soluble base and (2) at least one hydroxide compound chosen from alkali metal hydroxides, alkaline earth metal hydroxides, transition metal hydroxides, lanthanide metal hydroxides, actinide metal hydroxides, Group III hydroxides, Group IV hydroxides, Group V hydroxides, Group VI hydroxides, organic hydroxides, and compounds comprising at least one hydroxide substituent which is at least partially hydrolyzable, with the proviso that the at least one hydroxide compound is not sodium hydroxide, lithium hydroxide or potassium hydroxide. The multicompartment kit of this embodiment must contain at least one activating agent, at least one compound capable of being converted in situ to at least one soluble base and at least one hydroxide compound, but the at least one compound capable of being converted in situ and the at least one hydroxide compound may be found either both in the first compartment, both in the second compartment, or one in each of the compartments.

According to the present invention, the at least one compound capable of being converted in situ to at least one soluble base and the at least one hydroxide compound may be added just prior to use to form a composition that is applied to the hair, either simultaneously with or subsequent to combination with the at least one activating agent.

Further, any of the aforementioned compositions according to the present invention can be, for example, in the form of a dry powder or a liquid prior to being admixed with any other compositions of the present invention. For example, the at least one activating agent can be in crystalline form or can be in liquid form (such as dispersed in at least one solvent such as water and appropriately sealed against aerial oxidation).

The composition of the present invention may further comprise at least one suitable additive chosen from additives commonly used in hair relaxing compositions. Non-limiting examples of the at least one suitable additive include dyes, anionic surfactants, cationic surfactants, nonionic surfactants, amphoteric surfactants, fragrances, silicones, silicone derivatives, screening agents, preserving agents, proteins, vitamins, polymers such as thickening polymers, plant oils, mineral oils, synthetic oils and any other additive conventionally used in compositions for the care and/or treatment of hair.

Needless to say, a person skilled in the art will take care to select the at least one suitable additive such that the advantageous properties of the composition in accordance with the invention are not, or are not substantially, adversely affected by the addition(s) envisaged.

After a sufficient period of time to lanthionize the hair, the lanthionization is terminated when a desired level of relaxation of the keratin fibers has been reached. The lanthionizing composition may then be removed from the hair, such as, for example, by rinsing with water. A post-lanthionizing shampoo may then be applied, if desired, to clean the hair and remove any remaining composition from the hair or scalp. Suitable post-lanthionizing shampoos include those conventional shampoos typically used by those of skill in the art. For example, the post-lanthionizing shampoo may be a neutralizing shampoo having a pH ranging from acidic pH to neutral pH.

The compositions of the present invention may further comprise at least one complexing agent effective for dissociating the at least one hydroxide compound in an amount sufficient to effect lanthionization of keratin fibers. The at least one complexing agent may be an agent, such as a chelating agent or a sequestering agent, that leads to a partial or full dissociation of the at least one hydroxide compound. The at least one complexing agent may chelate, sequester or otherwise tie up the counter ion of the at least one hydroxide compound, allowing more available hydroxide ions to be liberated. Of course, the at least one complexing agent may do both. In any event, the net effect of the use of at least one complexation agent in accord with the present invention is the generation of enough available hydroxide ions to effect lanthionization of keratin fibers without relying on precipitation of a counter ion, such as $Ca^{++}$ in the form of $CaCO_3$.

The at least one complexing agent and the counter ion may form a complex that, in most cases, has stronger interactions than do the counter ion and the available hydroxide ion. As a result, the at least one complexing agent effectively removes the counter ion from the reaction medium and allows the equilibrium to be shifted to the right.

In a multicomponent kit, for example, the at least one activating agent may be formulated with the component comprising at least one hydroxide compound or with the component comprising at least one complexing agent or itself may be a third component that is combined with one or both of the component comprising at least one hydroxide compound and the component comprising at least one complexing agent.

In one embodiment, the at least one complexing agent of the present invention may be chosen from chelating agents, sequestering agents and salts of any of the foregoing. A chelating agent is a compound or ligand that can bind to a metal ion, usually through more than one ligand atom, to form a chelate. See Lewis, R. J., *Hawley's Condensed Chemical Dictionary* p. 240 (1997). A chelate is usually a type of coordination compound in which a central metal ion, such as $Co^{2+}$, $Ni^{2+}$, $Cu^{2+}$, $Ca^{2+}$ or $Zn^{2+}$, is attached by coordinate links to two or more nonmetal atoms, i.e., ligands, in the same molecule. Non-limiting examples of common chelating agents include ethylene-diaminetetraacetic acid (EDTA), nitrilotriacetic acid and ethylenegylcol-bis (β-amino-ethyl ether)-N,N-tetraacetic acid.

Sequestering agents may be any material that prevents at least one ion from exhibiting its usual properties due to close combination with that material. See Zviak at 991. Certain phosphates, for example, form a coordination complex with metal ions in solution so that the usual precipitation reactions may be prevented. See Zviak at page 991. For example, calcium soap precipitates are not produced from hard water treated with certain phosphates or metaphosphates. See Zviak at page 991. Other non-limiting examples of sequestering agents include hydroxy carboxylic acids, such as gluconic acid, citric acid and tartaric acid. Id.

In addition, other non-limiting examples of chelating agents and sequestering agents include amino acids and crown ethers. In one embodiment, the at least one complexing agent is chosen from amino acids, such as monosodium glutamate, a known calcium chelator.

The at least one complexing agent may also be chosen from phosphates demonstrating chelating and/or sequestering properties and silicates demonstrating chelating and/or sequestering properties. Non-limiting examples of phosphates demonstrating chelating and/or sequestering properties include tripotassium phosphate and trisodium phosphate. Non-limiting examples of silicates demonstrating chelating and/or sequestering properties include disodium silicate and dipotassium silicate.

Other non-limiting examples of the at least one complexing agent that may be useful in the practice of the invention include organic acids and salts thereof. The cations that may be used to form the salts of organic acids of the present invention may be chosen from organic cations and inorganic cations. In one embodiment, the inorganic cations are chosen from potassium, sodium and lithium.

In another embodiment, the at least one complexing agent is chosen from mono-hydroxycarboxylic acids, dihydroxycarboxylic acids, polyhydroxycarboxylic acids, mono-aminocarboxylic acids, di-aminocarboxylic acids, poly-aminocarboxylic acids, mono-hydroxysulfonic acids, di-hydroxysulfonic acids, polyhydroxysulfonic acids, mono-hydroxyphosphonic acids, dihydroxyphosphonic acids, polyhydroxyphosphonic acids, mono-aminophosphonic acids, diaminophosphonic acids and polyaminophosphonic acids.

In a further embodiment, the at least one complexing agent is chosen from ethylene diamine tetraacetic acid (EDTA), N-(hydroxyethyl) ethylene diamine triacetic acid, aminotrimethylene phosphonic acid, diethylenetriaminepentaacetatic acid, lauroyl ethylene diamine triacetic acid, nitrilotriacetic acid, iminodisuccinic acid, tartaric acid, citric acid, N-2-hydroxyethyliminodiacetic acid and salts of any of the foregoing.

In a further embodiment, the at least one complexing agent is chosen from a salt of EDTA, such as sodium EDTA, lithium EDTA, potassium EDTA and guanidine EDTA. EDTA has a strong calcium binding constant over a wide range of pH. For example, tetrasodium EDTA generally solubilizes calcium hydroxide in aqueous media to give a clear solution. The use of at least one complexing agent, such as tetrasodium EDTA, that solubilizes the counter ion of the at least one hydroxide compound may offer the benefit of no "ashing." However, the use of one or more complexing agents that do not completely solubilize the counter ion but only form slightly-soluble or sparingly-soluble complexing agent-counter ion complexes is also within the practice of the invention.

In another embodiment, the at least one complexing agent may comprise at least one "soft" entity chosen from "soft" bases and "soft" cations and at least one anion chosen from chelating anions and sequestering anions. Non-limiting examples of "soft" cations include organic cations such as guanidine. Non-limiting examples of "soft" bases include amines such as monoethanolamine, diethanolamine and triethanolamine. Such a combination of at least one "soft" entity and at least one anion may be effective if the "soft" entity exists at a high enough pH to achieve straightening or relaxing of the hair fibers. For example, amino acids such as arginine may be used to neutralize EDTA to make a "soft" base/strong chelator pair.

Depending on the nature of the at least one complexing agent, the solubility of the complex formed between the at least one complexing agent and the counter ion of the at least one hydroxide compound in the reaction medium may vary. In one embodiment, the at least one complexing agent-counter ion complex is considered by one of ordinary skill in the art to be soluble in the reaction medium. In another embodiment, a composition of the invention provides for an at least one complexing agent-counter ion complex having a solubility in water of greater than 0.03% at 25° C. and at a pH of 7.0, such as greater than 1% at 25° C. and at a pH of 7.0.

As one of ordinary skill in the art would recognize, mixtures of complexing agents including mixtures of at least one chelating agent and at least one sequestering agent are also within the practice of the invention. In one embodiment, a less active chelating agent, such as pentasodium aminotrimethylene phosphonate, may be mixed with a more active chelating agent, such as EDTA, to achieve a desired lanthionization of keratin fibers at a slower rate.

Other than in the operating example, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. The following examples are intended to illustrate the invention without limiting the scope as a result. The percentages are given on a weight basis. All instances of cysteine in the following examples refer to cysteine in the form of a carboxylate salt.

EXAMPLE 1

Relaxers with Low Levels of Guanidine Carbonate

Natural kinky hair was relaxed using a commercial no-lye relaxer cream (5.71% by weight $Ca(OH)_2$) with an activator solution containing decreasing amounts of guanidine carbonate. Example 1(a) represents a commercial product (control).

TABLE 1

Relaxing Efficiency as a Function of Guanidine Carbonate Concentration

| | Weight % Guanidine Carbonate in final mixture | Moles of Available Hydroxide per g of Final Mixture | Relaxing Efficiency |
|---|---|---|---|
| 1(a) | 5.8 | $6.5 \times 10^{-4}$ | Control |
| 1(b) | 4.9 | $5.5 \times 10^{-4}$ | Same efficiency as Control |
| 1(c) | 4.1 | $4.6 \times 10^{-4}$ | Less efficient than Control |

The results demonstrated that the relaxing efficiency decreased as the concentration of guanidine carbonate was lowered. From these results, it can be said that a concentration of guanidine carbonate of greater than 4.1% by weight in the final mixture efficiently relaxed the hair.

EXAMPLE 2

Effect of Cysteine on Relaxing Efficiency

Under the conditions above for 1 (c) where the composition comprising 4.1% by weight guanidine carbonate in the final mixture was less efficient in terms of relaxing than the control (comprising 5.8% by weight guanidine carbonate), naturally kinky hair was relaxed using compositions comprising the same concentration of guanidine carbonate (4.1% by weight in the final mixture) as well as a varying amount of cysteine.

TABLE 2

Relaxing Efficiency as a Function of Cysteine Concentration

| | Weight % Guanidine Carbonate in final mixture | Moles of Available Hydroxide per g of Final Mixture | Moles of Cysteine per g of Final Mixture | Molar Ratio of Available Hydroxide to Cysteine | Relaxing Efficiency (compared to control)[1] |
|---|---|---|---|---|---|
| 2(a) | 4.1 | $4.6 \times 10^{-4}$ | $2.6 \times 10^{-5}$ | 17.7:1 | Less efficient |
| 2(b) | 4.1 | $4.6 \times 10^{-4}$ | $2.8 \times 10^{-5}$ | 16:1 | Less efficient |
| 2(c) | 4.1 | $4.6 \times 10^{-4}$ | $3.3 \times 10^{-5}$ | 14:1 | Same efficiency |
| 2(d) | 4.1 | $4.6 \times 10^{-4}$ | $3.8 \times 10^{-5}$ | 12:1 | Same efficiency |

TABLE 2-continued

Relaxing Efficiency as a Function of Cysteine Concentration

| | Weight % Guanidine Carbonate in final mixture | Moles of Available Hydroxide per g of Final Mixture | Moles of Cysteine per g of Final Mixture | Molar Ratio of Available Hydroxide to Cysteine | Relaxing Efficiency (compared to control)[1] |
|---|---|---|---|---|---|
| 2(e) | 4.1 | $4.6 \times 10^{-4}$ | $4.6 \times 10^{-5}$ | 10:1 | Same efficiency |
| 2(f) | 4.1 | $4.6 \times 10^{-4}$ | $5.7 \times 10^{-5}$ | 8:1 | Same efficiency |
| 2(g) | 4.1 | $4.6 \times 10^{-4}$ | $7.7 \times 10^{-5}$ | 6:1 | Same efficiency |
| 2(h) | 4.1 | $4.6 \times 10^{-4}$ | $1.1 \times 10^{-4}$ | 4.2:1 | Same efficiency |

[1] control = 1(a) above, containing 5.8% by weight guanidine carbonate and no cysteine The results demonstrated that, at a low guanidine carbonate concentration, a molar ratio of available hydroxide ions to cysteine ranging from approximately 14:1 to 4:1 was as efficient in relaxing hair as the control. Low concentrations of cysteine as in examples 2(a) and 2(b) resulted in less efficient relaxing as compared to the control.

Therefore, the presence of a sufficient amount of cysteine decreased the amount of guanidine carbonate (and therefore the concentration of available hydroxide ions) needed to relax hair as efficiently as the control. Specifically, when 4.1% by weight guanidine carbonate and a sufficient amount of cysteine was used, the concentration of available hydroxide ions was decreased by 29% as compared to the control which contained 5.8% by weight guanidine carbonate and no cysteine. Further, the relaxing efficiency for 2(c) through 2(h) remained the same as the control, even with the lower percentage by weight of guanidine carbonate, due to the presence of a sufficient amount of cysteine.

EXAMPLE 3

Effect of Guanidine Carbonate Concentration on Relaxing Efficiency

Using a molar ratio of available hydroxide ions to cysteine of 4:1, naturally kinky hair was treated with compositions that contained a decreasing concentration of guanidine carbonate in the final mixture.

TABLE 3

Relaxing Efficiency as a Function of Guanidine Carbonate Concentration

| | Molar Ratio of Available Hydroxide to Cysteine | Weight % Guanidine Carbonate in final mixture | Relaxing Efficiency (compared to control) |
|---|---|---|---|
| 3(a) | no cysteine | 5.8 | Control (no cysteine) |
| 3(b) | 4:1 | 4.15 | Same efficiency |
| 3(c) | 4:1 | 3.3 | Same efficiency |
| 3(d) | 4:1 | 2.7 | Same efficiency |
| 3(e) | 4:1 | 1.8 | Less efficient |

The results demonstrated that where cysteine is present, particularly in a molar ratio of available hydroxide ions to cysteine of 4:1, the hair is efficiently relaxed even when treated with compositions comprising a low concentration of guanidine carbonate, i.e., lower than the 4.1% discussed in Examples 1 and 2. In order to maintain comparable efficiency with the control, a concentration of guanidine carbonate of 2.7% in the final mixture is sufficient.

EXAMPLE 4

Mechanical Strength of Relaxed Hair

Naturally kinky hair was relaxed with various no-lye compositions comprising cysteine. The relaxing efficiency of the compositions was determined and the resulting mechanical properties of hair relaxed using these compositions were measured using an Instron Tensile Tester.

TABLE 4

Mechanical Strength of Relaxed Hair as a Function of the Molar Ratio of Available Hydroxide to Cysteine

| | Molar Ratio of Available Hydroxide to Cysteine | Relaxing Efficiency | Elongation to Break (%) | Force to Break (g) |
|---|---|---|---|---|
| 4(a) | — | — | 80.37 | 49.67 |
| 4(b) | 8:1 | same efficiency | 82.81 | 53.6 |
| 4(c) | 5.8:1 | same efficiency | 82.99 | 53.69 |
| 4(d) | 4.2:1 | same efficiency | 16.29 | 25.17 |

The results demonstrated that, compared to a commercial no-lye relaxer (4(a)), a composition comprising a molar ratio of available hydroxide ions to cysteine of both 8:1 (Example 4(b)) and 5.8:1 (Example 4(c)) have similar relaxing efficiency and similar tensile properties of the hair result. It was also observed that a composition comprising a molar ratio of hydroxide to cysteine of 4.2:1 (Example 4(d)) had a relaxing efficiency similar to that of the commercial relaxer but the increased concentration of cysteine apparently damaged the hair.

What is claimed is:

1. A method for lanthionizing keratin fibers to achieve a desired relaxation comprising:
   (a) storing a first composition,
   (b) storing a second composition separately from said first composition,
   (c) combining said first composition with said second composition, and
   (d) applying said composition to said keratin fibers for a sufficient period of time to achieve a desired relaxation, wherein said first composition comprises at least one activating agent chosen from cysteine-based compounds and optionally at least one entity chosen from:
(1) at least one compound capable of being converted in situ to at least one soluble base; and
(2) at least one hydroxide compound with the proviso that said at least one hydroxide compound is not sodium hydroxide, lithium hydroxide or potassium hydroxide;
and wherein said second composition comprises at least one entity chosen from:
(1) at least one compound capable of being converted in situ to at least one soluble base; and
(2) at least one hydroxide compound with the proviso that said at least one hydroxide compound is not sodium hydroxide, lithium hydroxide or potassium hydroxide,
with the proviso that said at least one compound capable of being converted in situ to at least one soluble base and at least one hydroxide compound are present, together or separately, in at least one composition chosen from said first composition and said second composition.

2. A method according to claim 1, wherein said at least one activating agent is chosen from cysteine, optionally substituted; homologs of cysteine, optionally substituted; derivatives of cysteine, optionally substituted; and salts of any of the foregoing chosen from carboxylate salts, amine salts and mixtures thereof.

3. A method according to claim 2, wherein said at least one activating agent is cysteine.

4. A method according to claim 1, wherein said at least one activating agent is chosen from cysteine-based compounds which comprise at least one unsubstituted thiol group and cysteine-based compounds which comprise at least one protected thiol group wherein said at least one protected thiol group is de-protected upon hydrolysis.

5. A method according to claim 1, wherein said at least one compound capable of being converted in situ to at least one soluble base is guanidine carbonate, and wherein said at least one soluble base is unsubstituted guanidine hydroxide.

6. A method according to claim 1, wherein said at least one hydroxide compound is chosen from alkali metal hydroxides, alkaline earth metal hydroxides, transition metal hydroxides, lanthanide metal hydroxides, actinide metal hydroxides, Group III hydroxides, Group IV hydroxides, Group V hydroxides, Group VI hydroxides, and organic hydroxides.

7. A method according to claim 6, wherein said at least one hydroxide compound is calcium hydroxide.

8. A method according to claim 1, wherein said composition further comprises at least one complexing agent effective for dissociating the at least one hydroxide compound in a sufficient quantity to effect lanthionization of keratin fibers.

9. A method for lanthionizing keratin fibers comprising:
(a) storing a first composition,
(b) storing a second composition separately from said first composition,
(c) storing a third composition separately from said first composition and said second composition,
(d) combining said first composition with said second composition and said third composition, and
(e) applying said composition to said keratin fibers for a sufficient period of time to achieve a desired relaxation,
wherein said first composition comprises at least one activating agent chosen from cysteine-based compounds,
wherein said second composition is chosen from at least one compound capable of being converted in situ to at least one soluble base, and
wherein said third composition comprises at least one hydroxide compound, with the proviso that said at least one hydroxide compound is not sodium hydroxide, lithium hydroxide or potassium hydroxide.

10. A method according to claim 9, wherein said at least one activating agent is chosen from cysteine, optionally substituted; homologs of cysteine, optionally substituted; derivatives of cysteine, optionally substituted; and salts of any of the foregoing chosen from carboxylate salts, amine salts and mixtures thereof.

11. A method according to claim 9, wherein said at least one activating agent is cysteine.

12. A method according to claim 9, wherein said at least one activating agent is chosen from cysteine-based compounds which comprise at least one unsubstituted thiol group and cysteine-based compounds which comprise at least one protected thiol group wherein said at least one protected thiol group is de-protected upon hydrolysis.

13. A method according to claim 9, wherein said at least one compound capable of being converted in situ to at least one soluble base is guanidine carbonate, and wherein said at least one soluble base is unsubstituted guanidine hydroxide.

14. A method according to claim 9, wherein said at least one hydroxide compound is chosen from alkali metal hydroxides, alkaline earth metal hydroxides, transition metal hydroxides, lanthanide metal hydroxides, actinide metal hydroxides, Group III hydroxides, Group IV hydroxides, Group V hydroxides, Group VI hydroxides, and organic hydroxides.

15. A method according to claim 14, wherein said at least one hydroxide compound is calcium hydroxide.

16. A method according to claim 9, wherein said composition further comprises at least one complexing agent effective for dissociating the at least one hydroxide compound in a sufficient quantity to effect lanthionization of keratin fibers.

17. A multicompartment kit for lanthionizing keratin fibers to achieve relaxation of said keratin fibers comprising at least three compartments,
wherein a first compartment comprises at least one hydroxide compound, with the proviso that said at least one hydroxide compound is not sodium hydroxide, lithium hydroxide or potassium hydroxide,
wherein a second compartment comprises at least one compound capable of being converted in situ to at least one soluble base, and
wherein a third compartment comprises at least one activating agent chosen from cysteine-based compounds.

18. A multicompartment kit according to claim 17, wherein said at least one activating agent is cysteine.

19. A multicompartment kit according to claim 17, wherein said at least one compound capable of being converted in situ to at least one soluble base is guanidine carbonate, and wherein said at least one soluble base is unsubstituted guanidine hydroxide.

20. A multicompartment kit according to claim 17, wherein said at least one hydroxide compound is chosen from alkali metal hydroxides, alkaline earth metal hydroxides, transition metal hydroxides, lanthanide metal hydroxides, actinide metal hydroxides, Group III hydroxides, Group IV hydroxides, Group V hydroxides, Group VI hydroxides, and organic hydroxides.

21. A multicompartment kit according to claim 17, wherein said at least one hydroxide compound is calcium hydroxide.

22. A multicompartment kit for lanthionizing keratin fibers to achieve relaxation of said keratin fibers comprising at least two compartments,
- wherein a first compartment comprises at least one activating agent chosen from cysteine-based compounds and optionally at least one entity chosen from:
  (1) at least one compound capable of being converted in situ to at least one soluble base; and
  (2) at least one hydroxide compound, with the proviso that said at least one hydroxide compound is not sodium hydroxide, lithium hydroxide or potassium hydroxide; and
- wherein a second compartment comprises at least one entity chosen from:
  (1) at least one compound capable of being converted in situ to at least one soluble base; and
  (2) at least one hydroxide compound, with the proviso that said at least one hydroxide compound is not sodium hydroxide, lithium hydroxide or potassium hydroxide;
- with the proviso that said multicompartment kit comprises at least one activating agent, at least one compound capable of being converted in situ to at least one soluble base and at least one hydroxide compound.

23. A multicompartment kit according to claim 22, wherein said at least one activating agent is cysteine.

24. A multicompartment kit according to claim 22, wherein said at least one compound capable of being converted in situ to at least one soluble base is guanidine carbonate, and wherein said at least one soluble base is unsubstituted guanidine hydroxide.

25. A multicompartment kit according to claim 22, wherein said at least one hydroxide compound is chosen from alkali metal hydroxides, alkaline earth metal hydroxides, transition metal hydroxides, lanthanide metal hydroxides, actinide metal hydroxides, Group III hydroxides, Group IV hydroxides, Group V hydroxides, Group VI hydroxides, and organic hydroxides.

26. A multicompartment kit according to claim 22, wherein said at least one hydroxide compound is calcium hydroxide.

* * * * *